United States Patent
Fraas et al.

(10) Patent No.: US 10,682,471 B2
(45) Date of Patent: Jun. 16, 2020

(54) MULTI-PART SAFETY DEVICE FOR A SYRINGE

(71) Applicant: Gerresheimer Regensburg GmbH, Regensburg (DE)

(72) Inventors: Andreas Fraas, Amberg (DE); Maximilian Vogl, Mantel (DE)

(73) Assignee: Gerresheimer Regensburg GmbH, Regensburg (DE)

( * ) Notice: Subject to any disclaimer, the term of this patent is extended or adjusted under 35 U.S.C. 154(b) by 217 days.

(21) Appl. No.: 15/573,041

(22) PCT Filed: May 13, 2016

(86) PCT No.: PCT/EP2016/060863
§ 371 (c)(1),
(2) Date: Nov. 9, 2017

(87) PCT Pub. No.: WO2016/206862
PCT Pub. Date: Dec. 29, 2016

(65) Prior Publication Data
US 2018/0126091 A1    May 10, 2018

(30) Foreign Application Priority Data

Jun. 26, 2015  (DE) .................. 10 2015 110 343

(51) Int. Cl.
*A61M 5/32* (2006.01)

(52) U.S. Cl.
CPC .......... *A61M 5/326* (2013.01); *A61M 5/3271* (2013.01); *A61M 5/3272* (2013.01);
(Continued)

(58) Field of Classification Search
CPC .. A61M 5/326; A61M 5/3245; A61M 5/3271; A61M 5/3272; A61M 5/3202;
(Continued)

(56) References Cited

U.S. PATENT DOCUMENTS

| 5,591,138 A | 1/1997 | Vaillancourt |
| 6,238,371 B1 | 5/2001 | Himbert et al. |

(Continued)

FOREIGN PATENT DOCUMENTS

| DE | 112009001083 T5 | 3/2011 |
| WO | 2009/137845 | 11/2009 |
| WO | WO 2013/134465 A1 | 9/2013 |

OTHER PUBLICATIONS

Japanese Notice of Rejection, dated Oct. 4, 2018, in Japanese Patent Application No. 2007-559506, a related application, 5 pp. (In Japanese language).

(Continued)

*Primary Examiner* — Nathan R Price
*Assistant Examiner* — Melissa A Snyder
(74) *Attorney, Agent, or Firm* — Leydig, Voit & Mayer, Ltd.

(57) ABSTRACT

The invention relates to a safety device for a syringe for avoiding stab wounds, said syringe to having a syringe body and a piercing means arranged on the distal end of the syringe body. The safety device comprises a sleeve element (6) that extends along an axial direction (X) and encloses at least partly the piercing means and the syringe body, said sleeve element being rotatably mounted on a distal end region of the syringe body. The safety device is characterized by comprising a contact element (7) which contacts the skin of a patient when the syringe is used, said contact element being arranged on the distal end of the sleeve element and being rotatable independent of the sleeve element.

13 Claims, 4 Drawing Sheets

(52) U.S. Cl.
CPC ... *A61M 5/3221* (2013.01); *A61M 2005/3267* (2013.01); *A61M 2205/02* (2013.01)

(58) Field of Classification Search
CPC .. A61M 2005/3247; A61M 2005/3267; A61M 2005/208
See application file for complete search history.

(56) References Cited

U.S. PATENT DOCUMENTS

| | | |
|---|---|---|
| 2011/0137261 A1 | 6/2011 | Garber et al. |
| 2012/0041368 A1* | 2/2012 | Karlsson ............... A61M 5/326 604/111 |
| 2014/0228772 A1* | 8/2014 | Ward .................... A61M 5/326 604/198 |
| 2015/0157808 A1* | 6/2015 | Srinivasan .......... A61M 5/3202 604/198 |

OTHER PUBLICATIONS

International Search Report with Written Opinion corresponding to International Patent Application No. PCT/EP2016/060863, dated Aug. 2, 2016.

* cited by examiner

MULTI-PART SAFETY DEVICE FOR A SYRINGE

CROSS-REFERENCE TO RELATED APPLICATIONS

This application is a U.S. National Stage Application filed under 35 U.S.C. § 371 of International Application No. PCT/EP2016/060863, filed May 13, 2016, which claims the benefit of German Application No. DE 10-2015-110343.5, filed Jun. 26, 2015. Both of these applications are hereby incorporated by reference in their entireties.

The invention relates to a safety device for avoiding stab wounds for a syringe having a syringe body and a piercing means arranged at the distal end of the syringe body, comprising a sleeve element which extends in an axial direction (X) and at least partially encloses the piercing means and the syringe body, it being possible for the sleeve element to be rotatably arranged on a distal end region of the syringe body.

Generic safety devices for avoiding stab wounds are known from the prior art. The use of safety devices of this kind is expedient in particular in the case of pre-filled syringes. The handling of such syringes is very simple, as the medium does not have to be transferred to the syringe prior to use. Furthermore, the likelihood of using an incorrect medicine is very low, even in emergencies. For vaccines and countless other medicines they are now the first-choice primary packaging material. These syringes are usually manufactured from glass or plastics material (for example COC, COP) and have to be equipped with protective caps in order to prevent damage to and/or contamination of the cannula before the syringe is used. Moreover, it is important to secure the cannula after the syringe has been used, in order to avoid stab wounds. In this case, careless replacement of the protective cap on the cannula can cause stab wounds. Often, the corresponding protective cap can no longer be found, or replacement of said cap is forgotten, which results in an avoidable risk of injury.

Accordingly, needle guards have been developed that are rigidly connected to the syringe and automatically receive the needle again after the syringe has been used. A needle guard of this kind is disclosed in DE 11 2009 001 083 T5 for example. This document discloses a spring-driven safety sleeve which, when extended, surrounds the cannula and prevents said cannula from causing injury to the user. The safety sleeve has a curved track in which at least one guide pin moves, as a result of which it is possible to achieve different positions of the safety sleeve according to the needle tip.

In this case, the at least one guide pin has to be fastened to the front geometry of the syringe by means of a collar, or has to be rigidly connected to the syringe in another manner. In order to preclude tampering or incorrect use, it should not be possible, or it should be possible only with difficulty, to remove the collar comprising the guide pin from the syringe comprising a cannula. Accordingly, a correspondingly secure fit in the axial direction is necessary.

This results in the problem that, when there is a secured guide pin, the safety sleeve undergoes some degree of rotation about the longitudinal axis of the syringe body on account of the curved track. The resulting rotation of the safety sleeve located on the patient's skin is perceived by the patient as uncomfortable, since the rotation of the safety sleeve twists the skin around the puncture site.

In order to solve this problem, for example safety devices comprising a guide track and a guide pin that is guided therein have been developed. In order to now prevent rotation of the sleeve element comprising the guide track, the guide pin has been rotatably fastened to the syringe body. A safety device of this kind is disclosed in WO 2013/134465 A1 for example. The pin is generally arranged on a collar element which is rotatably arranged on the distal end of the syringe body. In general, however, this is difficult to implement, since in particular syringes made of glass have significant tolerance variations in the front geometry. Furthermore, the corresponding collar element is usually suitable for being arranged only on specific front geometries of the syringe body, which limits the scope of application of the safety device. Moreover, a rotatable fit of the pin element, combined with protection against movement/detachment in the longitudinal direction of the syringe body, can be achieved only with difficulty in terms of production.

The object of the present invention is therefore that of providing a safety device for avoiding stab wounds for a syringe, which device solves the problems mentioned at the outset.

This object is achieved by a safety device for avoiding stab wounds for a syringe having a syringe body and a piercing means arranged at the distal end of the syringe body, comprising a sleeve element which extends in an axial direction (X) and at least partially encloses the piercing means and the syringe body, it being possible for the sleeve element to be rotatably arranged on a distal end region of the syringe body. The safety device is characterised in that it comprises a contact element which contacts a patient's skin when the syringe is used and which is arranged at the distal end of the sleeve element and is rotatable independently of the sleeve element.

Before the syringe is used, the piercing means is arranged in the sleeve element, with the result that the piercing means is protected from damage and contamination. In this context, a piercing means can be a cannula, a needle or a lancet. When the syringe is used, the piercing means emerges from the sleeve element. The contact element then rests on the patient's skin. According to the invention, a rotation of the sleeve element in order to make the piercing means emerge is not transferred to the contact element, since the contact element is rotatable independently of the sleeve element. In this case, the expression "rotatable independently" is to be understood to mean that the static friction between the sleeve element and the contact element is less than static friction between the patient's skin and the contact element. The sleeve element can thus rotate without this rotational movement being transferred to the contact element.

The contact element is preferably rotatable in a plane perpendicular to the axial direction (X). More preferably, the contact element is arranged on the sleeve element in this plane. In general, syringes are used in such a way that they are oriented perpendicularly to the skin surface during use. It is therefore advantageous for the contact element to rotate in a plane perpendicular to the axial direction (X), in order to prevent the rotation of the sleeve element from being transferred to the patient's skin.

The safety device preferably comprises a collar element, which can be arranged on the distal end region of the syringe body and fastens the safety device to the syringe body. The safety device is therefore rigidly arranged on the syringe body by means of the collar element. A collar element of this kind can have a simple design, since said element does not have to be rotatable relative to the syringe body. In particular in the case of syringes made of glass, which, due to the manufacture thereof, have relatively large tolerances in the syringe front geometry, the collar element can be designed to compensate for these tolerances and to thus ensure optimal fastening of the safety device. Furthermore, the collar element can be designed such that it is possible to fasten said element to syringes having different front geometries. In particular, plastics syringes from different manufacturers may have different front geometries of this kind. It would be conceivable to connect the collar element to the syringe body by means of a clamped connection, a clip-on connection, an adhesive connection or another kind of connection.

The collar element preferably comprises at least one guide projection, which engages in at least one guide track of the sleeve element.

It would also be conceivable, however, for at least one guide projection to be formed integrally with the syringe body in the distal end region of the syringe body, the at least one guide projection engaging in at least one guide track of the sleeve element. An embodiment of this kind is conceivable in particular in the case of plastics syringes.

According to a particularly preferred embodiment, the guide projection is guided in the at least one guide track of the sleeve element substantially in the axial direction (X) when the syringe body is moved relative to the sleeve element. When the syringe is being used, the syringe, together with the safety device, is pressed against the patient's skin. The movement of the syringe body relative to the sleeve element and the guidance of the guide projection in the guide track cause the sleeve element to rotate in a circumferential direction (U). The sleeve element thus preferably slides over the syringe body, as a result of which the piercing means passes through a corresponding opening in the sleeve element.

Advantageously, two diametrically opposed guide projections are provided on the collar element and/or on the distal end region. Accordingly, the sleeve element would also comprise two diametrically opposed guide tracks, in each of which a guide projection is guided. This would ensure particularly stable guidance of the sleeve element.

According to a preferred concept of the invention, the sleeve element comprises a distal end portion which comprises a circumferential guide groove. The contact element preferably further comprises a guide projection, which engages in the guide groove of the sleeve element. The contact element is thus locked on the sleeve element relative to the axial direction (X), and is still rotatable in a plane perpendicular to the axial direction (X). Moreover, it would be conceivable for the surfaces of the guide groove and/or of the guide projection to comprise a coating that reduces the friction between said two elements and/or increases the sliding ability. This would achieve a smooth rotation of the contact element.

According to a particularly preferred embodiment, the contact element is annular. The perpendicular bisectors of the annular contact element and of the opening of the sleeve element, through which the piercing means passes when the syringe is used, are preferably on top of one another. Accordingly, the piercing means passes through the centre of the annular contact element when the syringe is used.

According to a further preferred embodiment, the contact element comprises a front face that contacts the patient's skin when the syringe is used. Advantageously, this front face has a soft and/or smooth feel. The front face therefore does have a feel that is perceived as comfortable for the skin. Preferably, the contact element can be produced from a material of this kind that is perceived as comfortable for the skin. It would also be conceivable to provide the front face with a surface structure that has a pleasant feel, for example by means of coatings or the like.

According to a preferred embodiment, the collar element is substantially formed as a hollow circular cylinder. Preferably, the circular cylinder comprises a lateral surface, on which the at least one guide projection is arranged. Preferably, the at least one guide projection extends radially away from the lateral surface. Further preferably, the guide projection is formed as a circular cylinder or as a pin.

The syringe body is preferably designed as a hollow circular cylinder and has in its distal end region a conical end piece on which the piercing means is arranged. Preferably, a projection is formed on the conical end piece, in which projection a front face of the distal end of the collar element can engage, as a result of which the collar element, and thus the safety device, can be locked in the axial direction. Further preferably, the safety device is also substantially designed as a hollow circular cylinder.

The safety device preferably comprises at least one spring element, which is operatively connected to the syringe body and counteracts the movement of the syringe body relative to the sleeve element and/or the safety device. Accordingly, the piercing means remains inside the sleeve element until the intended use. During use, the sleeve element has to be moved counter to the spring force in order for the cannula to be able to pass through the opening of the sleeve element. The guidance of the guide projection in the guide track causes the sleeve element to rotate along the circumferential direction (U). After the syringe has been used, the sleeve element automatically slides over the piercing means again, driven by the spring force of the spring element, the sleeve element now rotating counter to the circumferential direction (U) on account of the guidance of the guide projection in the guide track. The user is thus protected from receiving stab wounds from the used contaminated cannula. The spring element preferably comprises a spiral spring. Other types of spring, however, are also conceivable, such as leg springs or torsion springs. It would furthermore be conceivable to form the spring element as an elastomer.

According to a further advantageous concept of the invention, the at least one guide track comprises a first and a second track region, which are separated from one another by a fictive separating line extending along the axial direction (X) of the syringe body, it being possible for the guide projection to be arranged in a starting position in the first track region and to be moved from the first track region into an end position in the second track region by passing the separating line when a distal end of the piercing element is arranged at the level of the distal opening of the sleeve element as the syringe body is moved relative to the sleeve element.

Accordingly, the guide projection can be moved from the first track region into the second track region. Said guide projection is moved when it passes a fictive separating line that separates the first and the second track regions from one another. If the guide projection is in the first track region, i.e. in a starting position, the syringe has not yet been actuated, i.e. the piercing means has not yet left the safety device. If the guide projection is in the second track region, the piercing means has already left the safety device, making injection possible. When transitioning from the first track region to the second track region, i.e. at the exact point when the guide projection passes the separating line, the distal end of the piercing means is at the level of the distal opening of the safety device.

The guide projection can preferably be moved, by means of a track of the second track region, from the second track region into an end region in which a movement of the sleeve element relative to the syringe body is at least limited, substantially along the axial direction (X). An embodiment of this kind at least limits, preferably prevents, further movement of the sleeve element relative to the syringe body. Accordingly, the piercing means is prevented from leaving the safety device again after the syringe has been used.

Other advantages, aims and properties of the present invention are explained with reference to the following description of the attached drawings. Similar components can have the same reference signs in the various embodiments.

In the drawings:

FIG. 1 is an isometric view of a syringe (2) comprising a safety device (1) for avoiding stab wounds. FIGS. 2 and 3 are each sectional views of a syringe (2) comprising a safety device (1).

Figure 1:
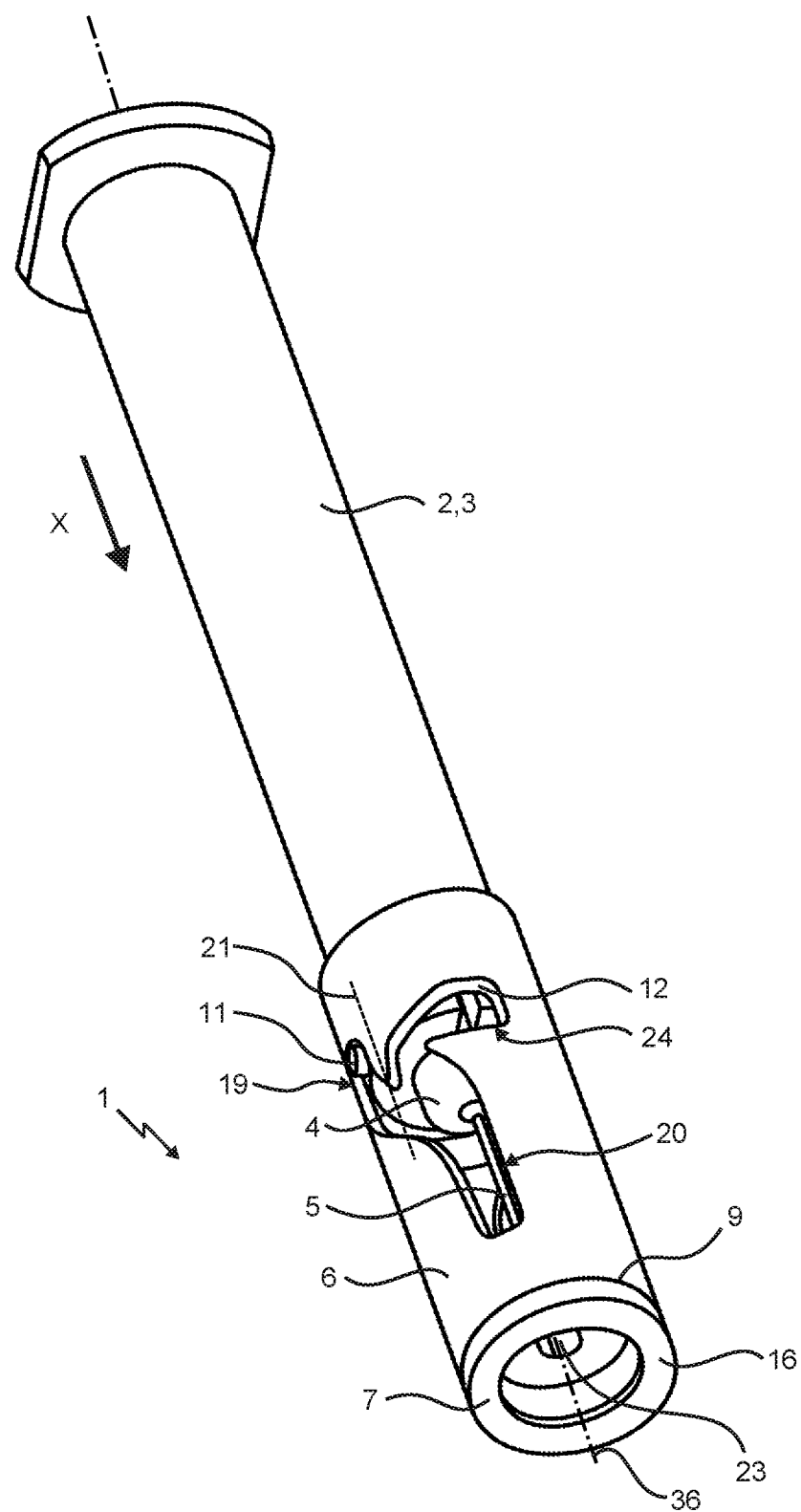
FIG. 1 is an isometric view of a syringe comprising a safety device.
Figure 2:
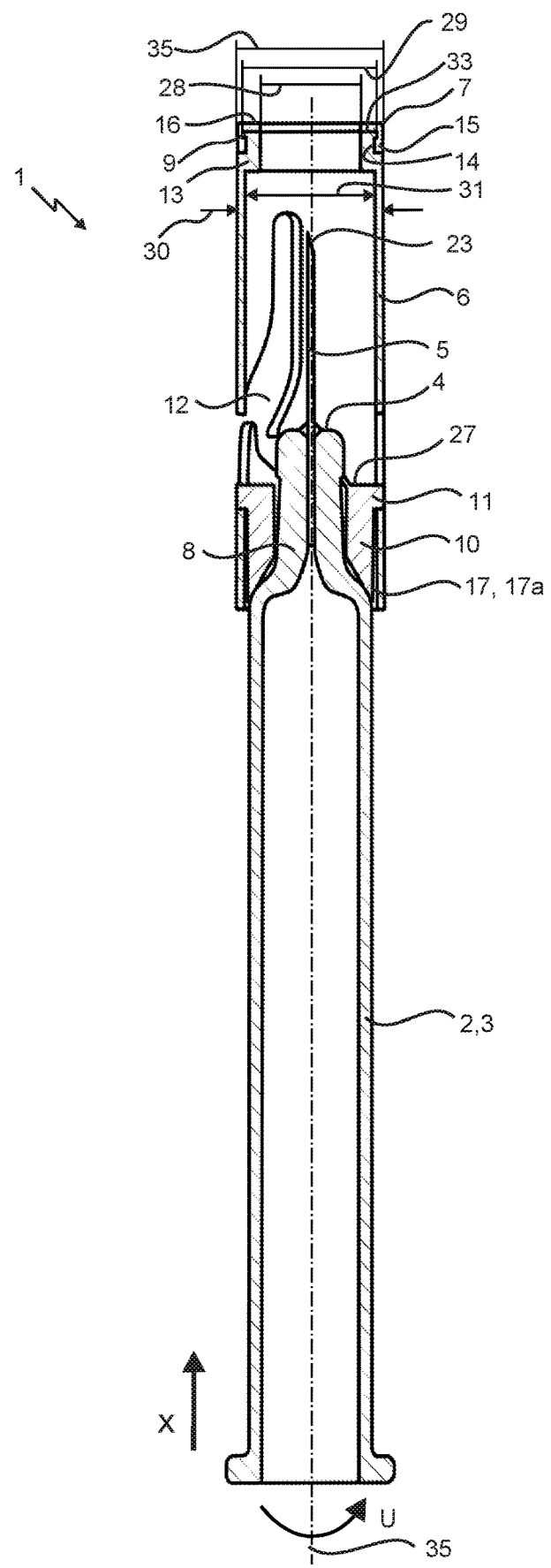
FIG. 2 is a sectional view of a syringe comprising a safety device.

The syringe (2) comprises a syringe body (3) designed as a hollow circular cylinder. The syringe body has a distal end region (8) comprising a distal end (4). A piercing means (5) is arranged at the distal end (4). This piercing means (5) is connected via a hole in the distal end region (8) to the cavity of the syringe body (3), so that the medium to be injected can emerge from the cavity through the piercing means (5) when the syringe (2) is used. The distal end region (8) is designed as a conical end piece which has a smaller external diameter than the syringe body (3). The syringe also has a transition region (25) in which the external diameter of the syringe body (3) transitions into the external diameter of the end piece.

The safety device (1) for avoiding stab wounds for a syringe (2) having a syringe body (3) and a piercing means (5) arranged at the distal end (4) of the syringe body (3) comprises a sleeve element (6) which extends along an axial direction (X) and at least partially encloses the piercing means (5) and the syringe body (3), it being possible for the sleeve element (6) to be rotatably arranged on a distal end region (8) of the syringe body (3). The safety device (1) comprises a contact element (7) which contacts a patient's skin when the syringe (2) is used and which is arranged at the distal end (9) of the sleeve element (6) and is rotatable independently of the sleeve element (6), the contact element (7) being rotatable in a plane perpendicular to the axial direction (X).

The safety device (1) further comprises a collar element (10) which can be arranged on the distal end region (8) of the syringe body (3). The safety device (1) is rigidly fastened to the syringe body (3) by means of the collar element (10). The collar element (10) is furthermore substantially formed as a hollow circular cylinder (17). The locking in the axial direction is made possible by a projection (26) or a thicker portion at the distal end (4) of the syringe body (3), on which projection or thicker portion the distal end (27) of the collar element (10) rests. The circular cylinder (17) further comprises a lateral surface (17a), on which two guide projections (11) are arranged. The guide projections (11) extend radially outwards from the lateral surface (17a), and are diametrically opposed to one another. Furthermore, said guide projections are formed as circular cylinders or as pins. These two guide projections (11) each engage in a guide track (12) of the sleeve element (6) and are guided therein substantially along the axial direction (X) when the syringe body (3) is moved relative to the sleeve element (6).

Figure 3:
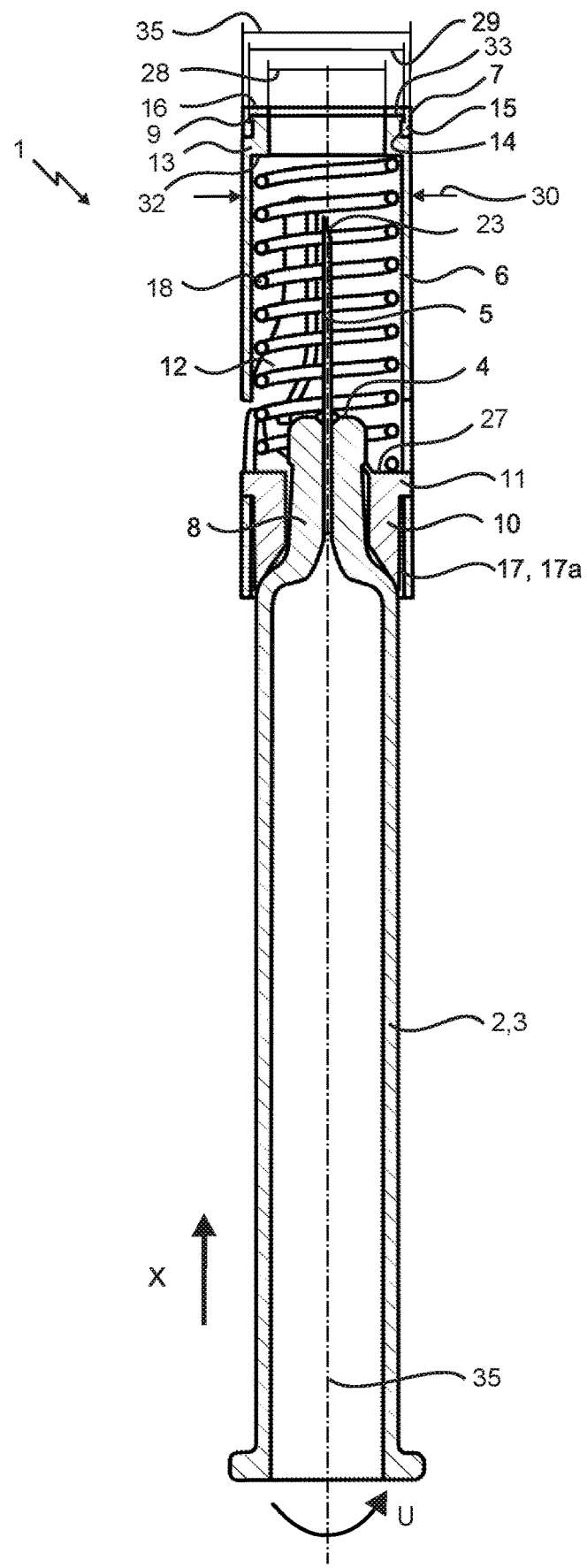
FIG. 3 is a sectional view of a syringe comprising a safety device.

FIG. 3 again shows a safety device (1), which comprises a spring element (18), in the form of a spiral spring, which is operatively connected to the syringe body (3) and counteracts the movement of the sleeve element (6) relative to the safety device (1).

Figure 4:
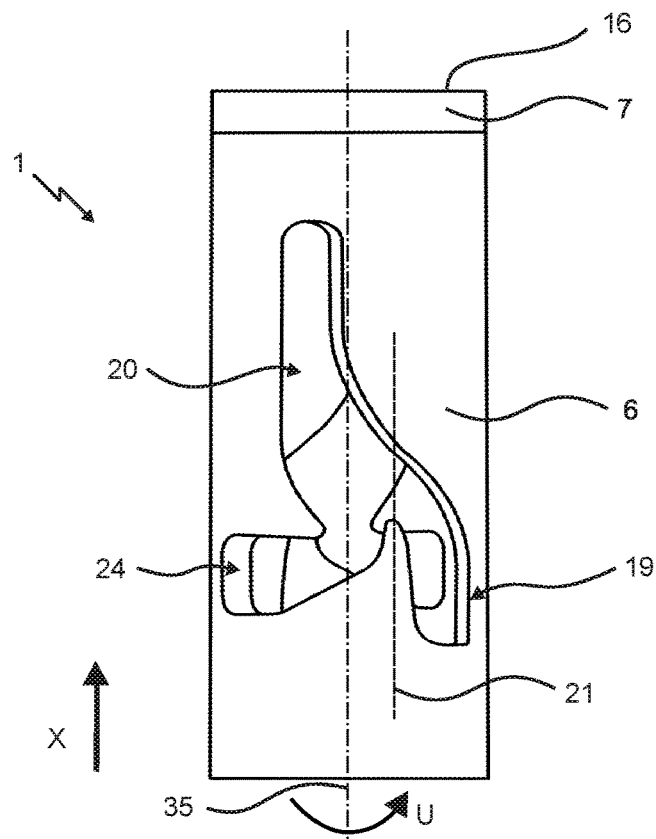
FIG. 4 is a side view of a safety device.
Figure 5:
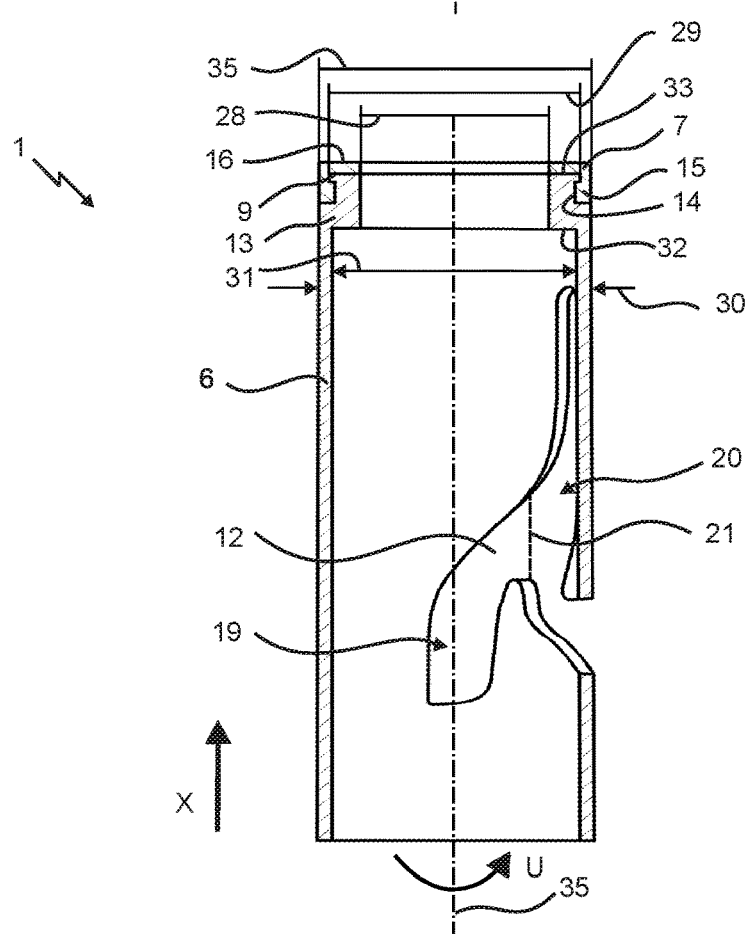
FIG. 5 is a sectional view of a safety device.

The sleeve element (6) and the contact element (7) are shown in detail in FIGS. 4 and 5, FIG. 4 being a side view and FIG. 5 being a sectional view of the sleeve element (6) and the contact element (7). The sleeve element (6) is substantially cylindrical and comprises a distal end portion (13) that has an internal diameter (28) and an external diameter (29). Both the internal diameter (28) and the external diameter (29) of the distal end portion (13) are smaller than an internal diameter (31) and an external diameter (30) of the adjacent portion of the sleeve element (6). Furthermore, the sleeve element (6) has a greater wall thickness in this distal end portion (13). This forms a contact surface (32) on which the spring element (18) rests in the axial direction (X). Furthermore, a guide groove (14) is formed in the lateral surface of the distal end portion (13).

The contact element (10) is annular and comprises a front face (16) that contacts a patient's skin when the syringe (2) is used. This front face (16) can have a soft and/or smooth feel, as a result of which said face is perceived as comfortable for the skin. The surface of the contact element (10) opposite the front face (16) rests on a front face (33) of the distal end portion (13). A guide extension (34), on which a guide projection (15) is arranged, extends from this opposite surface in the axial direction (X). This guide projection (15) engages in the circumferential guide groove (14) of the sleeve element. The guide extension (34) is designed such that the external diameter (35) of the contact element (7) corresponds to the external diameter (30) of the sleeve element (6). Furthermore, the central axes of the annular contact element (7) and the distal opening (23) of the sleeve element (6) are on top of one another, such that the piercing means passes through the centre of the annular contact element (7) when the syringe is used.

The piercing means (5) remains inside the sleeve element (6) until the intended use of the syringe (2). During use, the syringe is pressed against the patient's skin. The sleeve element (6) has to be moved counter to the spring force of the spring element (18) in order for the piercing means (5) to be able to pass through the distal opening (23) of the sleeve element (6) and through the annular contact element (7). In the process, the sleeve element is pushed over the distal end region (8) of the syringe body (3). The guidance of the guide projection (11) in the guide track (12) causes the sleeve element (6) to rotate along the circumferential direction (U). On account of the contact pressure, the static friction between the patient's skin and the contact element (7) is greater than the static friction between the contact element (7) and the sleeve element (6). Accordingly, the rotation of the sleeve element (6) is not transferred to the contact element (7) and/or to the patient's skin. After the syringe (2) has been used, the sleeve element (6) automatically slides over the piercing means (5) again, driven by the spring force of the spring element (22). The guidance of the guide projection (9) in the guide tracks (10) causes the sleeve element (6) to rotate counter to the circumferential direction (U), this rotation not being transferred to the patient's skin either, for the above-mentioned reasons. In the case of a rotation of this kind along or counter to the circumferential direction (U), the axis of rotation corresponds to the central axis (36) of the safety device.

In the embodiment shown, the guide tracks (12) of the sleeve element (6) comprise a first (19) and a second track region (20), which are separated from one another by a fictive separating line (21) extending along the axial direction (X) of the syringe body (3), it being possible for the guide projection (11) to be arranged in a starting position in the first track region (19) and to be moved from the first track region (19) into an end position in the second track region (20) by passing the separating line (25) when a distal end (22) of the piercing means (5) is arranged at the level of the distal opening (23) of the sleeve element (6) as the syringe body (3) is moved relative to the sleeve element (6).

The sleeve element (6) further comprises an end region (24). In this case, the guide projections (11) can be moved, by means of a track of the second track region (20), from the second track region (20) into an end region (24). In this end region (24), a movement of the sleeve element (6) relative to the syringe body (3) is at least limited, substantially along the axial direction (X).

All of the features disclosed in the application documents are claimed to be essential to the invention provided that they are novel over the prior art, either on their own or in combination with one another.

LIST OF REFERENCE SIGNS 1 safety device
2 syringe
3 syringe body
4 distal end of the syringe body
5 piercing means
6 sleeve element
7 contact element
8 distal end region of the syringe body
9 distal end of the sleeve element
10 collar element
11 guide projection
12 guide track
13 distal end portion of the sleeve element
14 guide groove
15 guide projection
16 front face of the contact element
17 circular cylinder
17a lateral surface of the circular cylinder
18 spring element
19 first track region
20 second track region
21 separating line
22 distal end of the piercing means
23 distal opening of the sleeve element
24 end region
25 transition region
26 projection
27 distal end of the collar element
28 internal diameter of the distal end portion
29 external diameter of the distal end portion
30 external diameter of the sleeve element
31 internal diameter of the sleeve element
32 contact surface
33 front face of the distal end portion
34 guide extension
35 external diameter of the contact element
36 central axis of the safety device
X axial direction
U circumferential direction
R radial direction

The invention claimed is:

1. A syringe body of a syringe comprising a piercing means arranged at its distal end, wherein said syringe body comprises a safety device for avoiding stab wounds arranged at the distal end of the syringe body, comprising a sleeve element which extends along an axial direction (X) and at least partially encloses the piercing means and the syringe body, the sleeve element comprising at least one guide track, a distal end portion and an adjacent proximal portion, wherein the sleeve element is arranged on a distal end region of the syringe body,
wherein the safety device comprises a collar element, by means of which the safety device is rigidly arranged on the distal end region of the syringe body, the safety device comprising a contact element which is able to contact a patient's skin when the syringe is used and which is arranged at the distal end of the sleeve element and is rotatable in a circumferential direction (U) independently of the sleeve element, as a result of which the rotation of the sleeve element is not transferred to the contact element, wherein the sleeve element has a greater wall thickness in said distal end region than in said adjacent proximal portion, wherein a circumferential guide groove being formed in a lateral surface of said distal end portion, and the contact element comprises a first guide projection which engages in the circumferential guide groove of the sleeve element,
wherein the collar element comprises at least one second guide projection, which engages in the at least one guide track of the sleeve element, wherein a movement along the axial direction (X) of the syringe body relative to the sleeve element and the guidance of the at least one second guide projection in the at least one guide track cause the sleeve element to rotate in the circumferential direction (U).

2. The safety device according to claim 1, wherein the contact element is rotatable in a plane perpendicular to the axial direction (X).

3. The safety device according to claim 1, wherein the contact element is annular.

4. The syringe body according to claim 1, wherein the contact element comprises a front face that contacts a patient's skin when the syringe is used.

5. The safety device according to claim 1, wherein the collar element is substantially formed as a hollow circular cylinder, the circular cylinder comprising a lateral surface, on which the at least one second guide projection is arranged.

6. The safety device according to claim 1, wherein the safety device comprises at least one spring element, which is operatively connected to the syringe body and counteracts the movement of the syringe body relative to the sleeve element.

7. The safety device according to claim 1, wherein the guide track comprises a first and a second track region, which are separated from one another by a fictive separating line extending along the axial direction (X) of the syringe body, it being possible for the at least one second guide projection to be arranged in a starting position in the first track region and to be moved from the first track region into an end position in the second track region by passing the separating line when a distal end of the piercing means is arranged at the level of the distal opening of the sleeve element as the syringe body is moved relative to the sleeve element.

8. The safety device according to claim 7, wherein the at least one second guide projection can be moved, by means of a track of the second track region, from the second track region into an end region in which a movement of the sleeve element relative to the syringe body is at least limited, substantially along the axial direction (X).

9. The safety device according to claim 1, wherein the guide track comprises a first and a second track region, which are separated from one another by a fictive separating line extending along the axial direction (X) of the syringe body, it being possible for the at least one second guide projection to be arranged in a starting position in the first track region and to be moved from the first track region into an end position in the second track region by passing the separating line when a distal end of the piercing means is arranged at the level of the distal opening of the sleeve element as the syringe body is moved relative to the sleeve element.

10. The safety device according to claim 9, wherein the at least one second guide projection can be moved, by means of a track of the second track region, from the second track region into an end region in which a movement of the sleeve element relative to the syringe body is at least limited, substantially along the axial direction (X).

11. The syringe body according to claim 1, wherein the distal end portion has an internal diameter and an external diameter, wherein the internal diameter of the distal end portion is smaller than an internal diameter of the adjacent portion of the sleeve element, and the external diameter of the distal end portion is smaller than an internal diameter and an external diameter of the adjacent portion of the sleeve element, wherein due to the said difference in the internal diameters and the enlarged wall thickness of the distal end portion a contact surface is formed on which the spring element rests in the axial direction (X).

12. The syringe body according to claim 1, wherein the during the application of the syringe the static friction between the sleeve element and the contact element is less than static friction between the patient's skin and the contact element.

13. The syringe body according to claim 1, wherein the surfaces of the guide track and/or of the at least one second guide projection comprise a coating that reduces the friction between said two elements and/or increases the sliding ability.

* * * * *